US010267761B2

(12) United States Patent
Wang et al.

(10) Patent No.: US 10,267,761 B2
(45) Date of Patent: Apr. 23, 2019

(54) MATERIAL FOR SENSING ELECTRODE OF $NO_X$ GAS SENSOR

(71) Applicant: DELPHI TECHNOLOGIES IP LIMITED, St. Michael (BB)

(72) Inventors: Da Yu Wang, Troy, MI (US); David M. Racine, Davison, MI (US); Yao Sheng, Troy, MI (US); Alfredo Ibarra Covarrubias, Oxford, MI (US)

(73) Assignee: DELPHI TECHNOLOGIES IP LIMITED (BB)

( * ) Notice: Subject to any disclaimer, the term of this patent is extended or adjusted under 35 U.S.C. 154(b) by 279 days.

(21) Appl. No.: 15/181,582

(22) Filed: Jun. 14, 2016

(65) Prior Publication Data
US 2017/0356873 A1 Dec. 14, 2017

(51) Int. Cl.
*G01N 27/407* (2006.01)
*G01N 33/00* (2006.01)

(52) U.S. Cl.
CPC ..... *G01N 27/4075* (2013.01); *G01N 27/4071* (2013.01); *G01N 27/4074* (2013.01); *F01N 2560/026* (2013.01); *G01N 33/0037* (2013.01)

(58) Field of Classification Search
CPC ............... G01N 27/406; G01N 27/407; G01N 27/4075; F01N 13/008
See application file for complete search history.

(56) References Cited

U.S. PATENT DOCUMENTS

| 6,019,881 A | 2/2000 | Kurosawa et al. |
| 6,849,239 B2 | 2/2005 | Morris |
| 2010/0084269 A1 | 4/2010 | Wang et al. |
| 2014/0004422 A1* | 1/2014 | Yang .................. H01M 4/5825 429/221 |
| 2016/0169831 A1 | 6/2016 | Wang et al. |

FOREIGN PATENT DOCUMENTS

EP 2975390 A1 1/2016

OTHER PUBLICATIONS

Sun et al, "Synthesis of MgMnSiO4 and its Application as Cathode Material for Magnesium Battery", Short Communication, Journal of New Materials for Electrochemical Systems, 17, 9-11 (2014) (Year: 2014).*
Sun, Sol-Gel Synthesis of Cathode Material MgSoSiO4 for Magnesium Cells, Asian Journal of Chemistry, vol. 24, No. 5 (2012), 1909-1911 (Year: 2012).*

* cited by examiner

*Primary Examiner* — Alexander S Noguerola
(74) *Attorney, Agent, or Firm* — Joshua M. Haines

(57) ABSTRACT

A $NO_2$ gas sensing element includes an electrolyte, a reference electrode in contact with the electrolyte, and a sensing electrode selective to $NO_2$ in contact with the electrolyte spaced apart from the reference electrode. The $NO_2$ selective sensing electrode includes an oxide material comprising: (1) a mixed oxide according to the formula $(Mn_{2-u-v-w}Co_vMg_w SiO_{4-u})+\xi(Mn_3Al_2Si_3O_{12})+\delta(SiO_2)$, wherein $0 \leq (u+v+w) \leq 2.0$, $0 \leq \xi \leq 0.5$, and $0 \leq \delta \leq 0.1$; (2) a mixed oxide according to the formula $(Mn_{2-x-y-z}Co_yMg_zSiO_{4-x})+\xi(ZnO)+\delta(SiO_2)$, wherein $0 \leq (u+v+w) \leq 2.0$, $0 \leq \xi \leq 0.5$, and $0 \leq \delta \leq 0.1$; or combinations of mixed oxides (1) and (2).

20 Claims, 5 Drawing Sheets

MATERIAL FOR SENSING ELECTRODE OF NO$_X$ GAS SENSOR

BACKGROUND

Combustion exhaust gas generated by furnaces, ovens, and diesel engines, contains nitrogen oxides (NO$_X$), which are detrimental to environment. These NOx need to be reduced to form non-harmful gases such as N$_2$, O$_2$, H$_2$O, before releasing to the ambient atmosphere. The NO$_X$ reduction can be accomplished by using ammonia gas (NH$_3$) generated by mixing urea with water in a reaction shown in following,

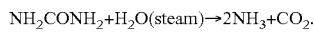

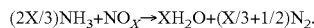

The water-mixed urea is injected into the exhaust stream before a selective catalytic reduction (SCR) converter where ammonia reduces NO and NO$_2$ to N$_2$ and H$_2$O before exhausting to the ambient atmosphere. NO and NO$_2$ have very different reduction rates with ammonia in the SCR converter. Therefore there is a need to know the individual amount of NO and NO$_2$, in the exhaust gas for NO$_X$ reduction control and on board diagnosis (OBD). Existing commercially available exhaust gas NO$_X$ sensors can detect a total amount of NO$_X$, but do not distinguish NO from NO$_2$. Additionally, these sensors do not distinguish NH$_3$ from NO$_X$ either. There is thus a need to have a NO$_2$ sensor that can sense NO$_2$ and be resistant to the interference sensing effect from NO and NH$_3$.

SUMMARY

In accordance with some example embodiments, a NO$_2$ gas sensing element comprises an electrolyte, a reference electrode in contact with the electrolyte, and a sensing electrode selective to NO$_2$ in contact with the electrolyte spaced apart from the reference electrode. The NO$_2$ selective sensing electrode comprises an oxide material comprising: (1) a mixed oxide according to the formula (Mn$_{2-u-v-w}$Co$_v$Mg$_w$SiO$_{4-u}$)+ξ(Mn$_3$Al$_2$Si$_3$O$_{12}$)+δ(SiO$_2$), wherein 0≤(u+v+w)≤2.0, 0≤ξ≤0.5, and 0≤δ≤0.1; (2) a mixed oxide according to the formula (Mn$_{2-x-y-z}$Co$_y$Mg$_z$SiO$_{4-x}$)+ξ(ZnO)+δ(SiO$_2$), wherein 0≤(x+y+z)≤2.0, 0≤ξ≤0.5, and 0≤δ≤0.1; or combinations comprising mixed oxides (1) and (2).

In accordance with some example embodiments, a NO$_2$ sensor comprises the NO$_2$ sensing element, a heating cell, a temperature-sensing cell, and an electrochemical NO$_2$ sensing cell comprising an electrical circuit connection between the sensing element reference and sensing electrodes and configured to contact the reference and sensing electrodes with test gas.

In accordance with some example embodiments, a combustion exhaust system comprises the NO$_2$ sensor disposed with the NO$_2$ sensing cell providing contact of the reference and sensing electrodes with a source of combustion exhaust gas, and an electronic controller in contact with sensor's heating cell, temperature-sensing cell, and electrochemical NO$_2$ sensing cell. The electronic controller is configured to provide close-loop control of the heating cell based on temperature-sensing cell output, and/or to convert emf data from the NO$_2$ sensing cell electrical circuit to NO$_2$ concentration value.

In some aspect of this invention, a process for measuring the concentration of NO$_2$ in a gas is provided using an NO$_2$ gas sensor in accordance with the above description. The gas to be measured is contacted with the reference and sensing electrodes; and a voltage signal is measured between the sensing electrode and the reference electrode.

BRIEF DESCRIPTION OF DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

The present disclosure relates to a NO$_2$ sensor for monitoring and measuring NO$_2$ gas in a gas stream such as exhaust gases in combustion systems, for example, internal combustion engines and furnaces. It is noted that, although the sensor is described in relation to a flat plate sensor, other sensor designs can also be employed, such as conical and the like.

The NO$_2$ sensing element can generate an emf as described by the Nernst Equation, particularly as adapted for use under non-equilibrium conditions. In the exemplary embodiment, the sample gas is introduced to the sensing electrode and is diffused throughout the porous electrode materials. In the sensing electrode, the materials induce electrochemical reactions in the sample gas. These reactions include catalyzing NO$_2$ to O$^{-2}$ and NO. Similarly, in the reference electrode, catalytic material induces electrochemical reactions at the reference electrode, converting equilibrium oxygen gas (O$_2$) to oxide ions (O$^{-2}$) or vice versa, and thereby producing an emf. Therefore, the electrical potential difference between the sensing electrode and the corresponding reference electrode can be measured to determine an emf.

The reactants at electrodes of the NO$_2$ sensing element may include NH$_3$, NO, NO$_2$, CO, HC, H$_2$O, and O$_2$. The partial pressure of reactive components at the electrodes of NO$_2$ sensing cell(s) can be determined from the cell's electromotive force (emf) by using the non-equilibrium Nemst Equation(1):

$$EMF \approx \frac{kT}{Ae}\text{Ln}(P_{NO}) - \frac{kT}{Be}\text{Ln}(P_{O_2}) - \qquad (1)$$

-continued
$$\frac{kT}{Ce}\text{Ln}(P_{H_2O}) - \frac{kT}{De}\text{Ln}(P_{NO_2}) - \frac{kT}{Ee}\text{Ln}(P_{NH_3}) + \text{constant}$$

where: k=the Boltzmann constant
T=the absolute temperature of the gas
e=the electron charge unit
A, B, C, D, E are constants
Ln=natural log
$P_{NH_3}$=the partial pressure of ammonia in the gas,
$P_{O_2}$=the partial pressure of oxygen in the gas,
$P_{NO_2}$=the partial pressure of nitrogen dioxide in the gas,
$P_{H_2O}$=the partial pressure of water vapor in the gas
$P_{NO}$=the partial pressure of nitrogen monoxide in the gas.
In many practical applications, the terms involving NO, $H_2O$, and $NH_3$ in above equation can be ignored as their effect is small compared with that of $NO_2$.

Figure 1:
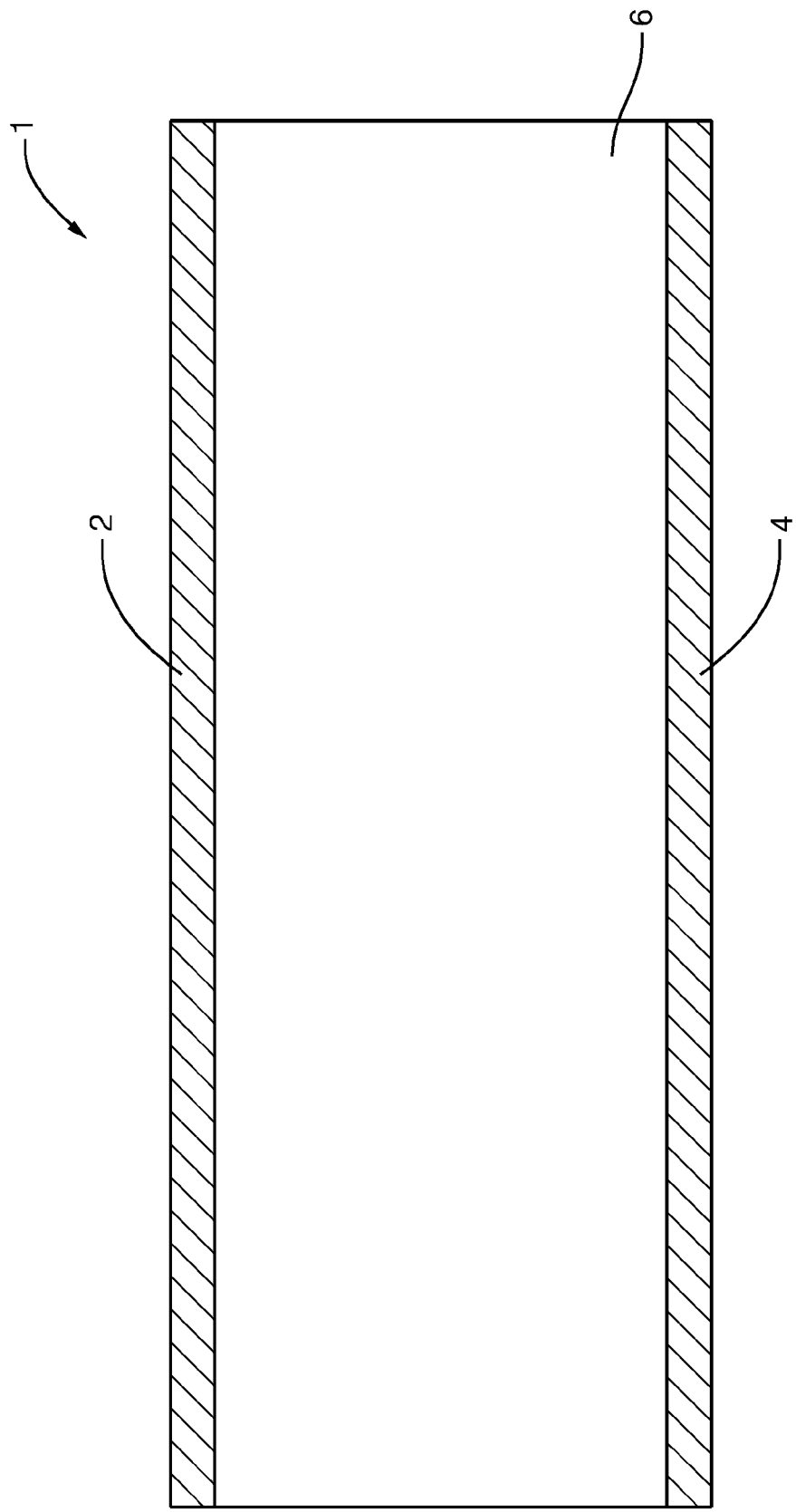
FIG. 1 is a cross-sectional view of an exemplary embodiment of a NO$_2$ sensing element

As mentioned above, a $NO_2$ sensing element can comprise an electrolyte, a reference element, and a sensing element. An example embodiment of a $NO_2$ sensing element is depicted in FIG. 1, where sensing element 1 has sensing electrode 2 and reference electrode 4 disposed on opposite sides of an electrolyte layer 6. The sensing electrode 2 and reference electrode 4 can be connected by an electrical circuit (not shown) configured for measurement of EMF differences between the electrodes.

Electrolytes for the sensing element typically conduct oxygen ions. In some embodiments, they can also provide fluid separation of molecular oxygen on each sides of an electrolyte layer such as electrolyte layer 6. The electrolyte layer can be any size capable of providing sufficient ionic communication for the $NO_2$ sensing element. The electrolyte can be the entire length and width of the sensing element or portions thereof. Any suitable electrolyte material having such characteristics may be used. Examples of potential electrolyte layer materials include solid oxides such as zirconium oxide (zirconia), cerium oxide (ceria), calcium oxide, yttrium oxide (yttria), lanthanum oxide, lanthanum gallates, magnesium oxide, alumina oxide (alumina), indium oxide and the like, as well as combinations comprising at least one of the foregoing electrolyte materials, such as yttria doped zirconia, $LaGaO_3$, $SrCeO_3$, $BaCeO_3$, and $CaZrO_3$. These electrolyte materials may also include various dopants, alloying additions or other modifiers used to promote, prevent, stabilize or otherwise produce a desired microstructural affect, such as, for example, zirconia which is stabilized with respect to, among others, polymorphism, high temperature phase transformation, and the like, by the addition of calcium, barium, yttrium, magnesium, aluminum, lanthanum, cesium, gadolinium, ytterbium, scandium, or the like, or oxides thereof. A solid electrolyte layer can be formed using any method available to one with ordinary skill in the art including, but not limited to, doctor blade slurry casting, tape casting, die pressing, roll compaction, stenciling, screen printing, and the like.

A reference electrode such as reference electrode 4 is disposed in physical contact and in ionic communication with the electrolyte layer 6, and can be disposed in fluid communication with the sample gas or reference gas, preferably with the sample gas. The reference electrode materials have oxygen catalyzing capability (e.g., catalyzing equilibrium $O_2$ gas to produce an emf), electrical conducting capability (conducting electrical current produced by the emf), and/or gas diffusion capability (providing sufficient open porosity so that gas can diffuse throughout the electrode and to the interface region of the reference electrode 4 and electrolyte 6). Possible reference electrode materials include platinum (Pt), palladium (Pd), osmium (Os), rhodium (Rh), iridium (Ir), gold (Au), ruthenium (Ru), and the like, as well as mixtures or alloys comprising at least one of the foregoing materials. The electrode can include metal oxides such as zirconia and alumina that can increase the electrode porosity and increase the contact area between the electrode and the electrolyte. With respect to the size and geometry of the reference electrode 4, it is generally adequate to provide current output sufficient to effect a reasonable signal resolution over a wide range of $NO_2$ concentrations. Generally, a thickness of about 1 to about 25 µm can be employed, more specifically a thickness of about 5 to about 20 µm, and even more specifically a thickness of about 10 to about 18 µm. In some embodiments, the porosity of the reference electrode can be adjusted to affect and contribute to contact of test gas with the noble metal by promoting diffusion between the gas phase and the electrode and electrolyte. The reference electrode 4 can be formed using any suitable technique such as chemical and/or physical vapor deposition, screen printing, sputtering, and stenciling, among others, in any combination, with screen printing of inks or pastes that include the electrode material onto appropriate tapes being advantageous due to simplicity, economy, and compatibility with the subsequent firing process. For example, reference electrode 4 can be screen printed onto an abutting layer or the solid electrolyte layer 6. Further, the reference electrode 4 can be embedded within the electrolyte or in other layers of a larger sensor structure.

As mentioned above, a $NO_2$ sensing electrode such as electrode 2 comprises an oxide material comprising: (1) a mixed oxide according to the formula $(Mn_{2-u-v-w}Co_vMg_wSiO_{4-u})+\xi(Mn_3Al_2Si_3O_{12})+\delta(SiO_2)$, wherein $0 \leq (u+v+w) \leq 2.0$, $0 \leq \xi \leq 0.5$, and $0 \leq \delta \leq 0.1$; (2) a mixed oxide according to the formula $(Mn_{2-x-y-z}Co_yMg_zSiO_{4-x})+\xi(ZnO)+\delta(SiO_2)$, wherein $0 \leq (x+y+z) \leq 2.0$, $0 \leq \xi \leq 0.5$, and $0 \leq \delta \leq 0.1$; or combinations comprising mixed oxides (1) and (2). In some embodiments, either of the mixed oxides (1) or (2), independently, or both of the mixed oxides together can be characterized by $0.75 \leq (u+v+w) \leq 1.25$, $0 \leq \xi \leq 0.025$, and $0 \leq \delta \leq 0.050$ with respect to the mixed oxide (1), or by $0.75 \leq (x+y+z) \leq 1.25$, $0 \leq \xi \leq 0.025$, and $0 \leq \delta \leq 0.050$ with respect to the mixed oxide (2).

The $NO_2$ sensing electrode materials may be made by any suitable method. In an exemplary embodiment, the sensing electrode material may be made by mixing powders of metal oxide precursors having the desired constituent elements in amounts sufficient to provide the desired stoichiometric composition. Metal oxide precursors can be metal oxides, or any material comprising the metal that can oxidize under during processing of the powders to form the sensing electrode, such as by sintering in air of the metal oxide precursor powder mixture to form the $NO_2$ sensing electrode material. By way of non-limiting example, powders for the mixed oxide (1) can include CoO MnO, $SiO_2$, MgO $Al_2O_3$ or $CoCO_3$, $MnCO_3$, $MgCO_3$. Powders for the mixed oxide (2) can include CoO MnO, $SiO_2$, ZnO, or $CoCO_3$, $MnCO_3$, $MgCO_3$, $ZnCO_3$.

The metal oxide precursors are used in an amount depending on the desired final microstructure and composition of the $NO_2$ sensing electrode material, and can be easily determined by a person of ordinary skill in the art. The metal oxide precursors are mixed using any suitable method to produce an intimate homogeneous mixture, such as by milling, by using a mortar and pestle, or the like. After mixing, the metal oxide precursor powders are heated to a temperature and for a time sufficient to form the desired $NO_2$ sensing electrode material composition. The heating may be done in air, but it is believed that for some combinations, heating other atmospheres or in vacuum may be desirable.

After the formation of the desired $NO_2$ sensing electrode material, it is disposed on the solid electrolyte. This can be effected using any suitable deposition application or other technique available to one with ordinary skill in the art including, but not limited to, spray coating, painting, dip coating, screen printing, laminating, and the like.

In one advantageous embodiment, disposing is effected by screen printing. In this embodiment, the $NO_2$ sensing electrode material can be made into an ink, which also refers to a paste or other fluid form suitable for screen printing, and disposed onto the solid electrolyte 6 or an insulating layer (22, FIG. 2) in contact solid electrolyte. The ink can further comprise a binder, a carrier, a wetting agent, and the like, and combinations comprising at least one of the foregoing. The binder can be any material capable of providing adhesion between the ink and the substrate. Non-limiting examples of binders include acrylic resin, acrylonitrile, styrene, poly(acrylic acid), poly(methacrylic acid), poly(methyl acrylate), poly(methyl methacrylate), and the like, as well as combinations comprising at least one of the foregoing binders. Carriers include any material suitable for imparting desired printing, drying, and rheological characteristics of the ink. Non-limiting examples of carriers include volatile solvents which can dissolve polymer resins such as butyl acetate. Non-limiting examples of wetting agents include ethanol, isopropyl alcohol, methanol, cetyl alcohol, and the like, as well as combinations comprising at least one of the foregoing.

The different constituents of the ink can be present in different amounts depending on the nature of the materials, and the product, and can be readily determined by a person with ordinary skill in the art. In general, the binder can be present in about 1 to about 40 wt %, the carrier can be present in about 1 to about 40 wt %, the wetting agent can be present in about 1 to about 20 wt %, and the $NO_2$ sensing electrode material can be present in about 15 to about 98 wt %, based on the total weight of the ink.

Fugitive materials can also be used in the ink formulations to produce a desired porosity in the final $NO_2$ sensing electrode, that is, a sufficient porosity to enable the $NO_2$ to enter the $NO_2$ sensing electrode and reach triple points (points where the electrode, electrolyte, and $NO_2$ meet to enable the desired electrochemical reactions). Fugitive materials are materials that degrade leaving voids upon firing. Some non-limiting examples of fugitive materials include graphite, carbon black, starch, nylon, polystyrene, latex, other soluble organics (e.g., sugars and the like), and the like, as well as combinations comprising one or more of the foregoing fugitive materials. The fugitive material can be present in an amount of about 0.1 to about 20 wt %, based on the total weight of the ink.

Figure 2:
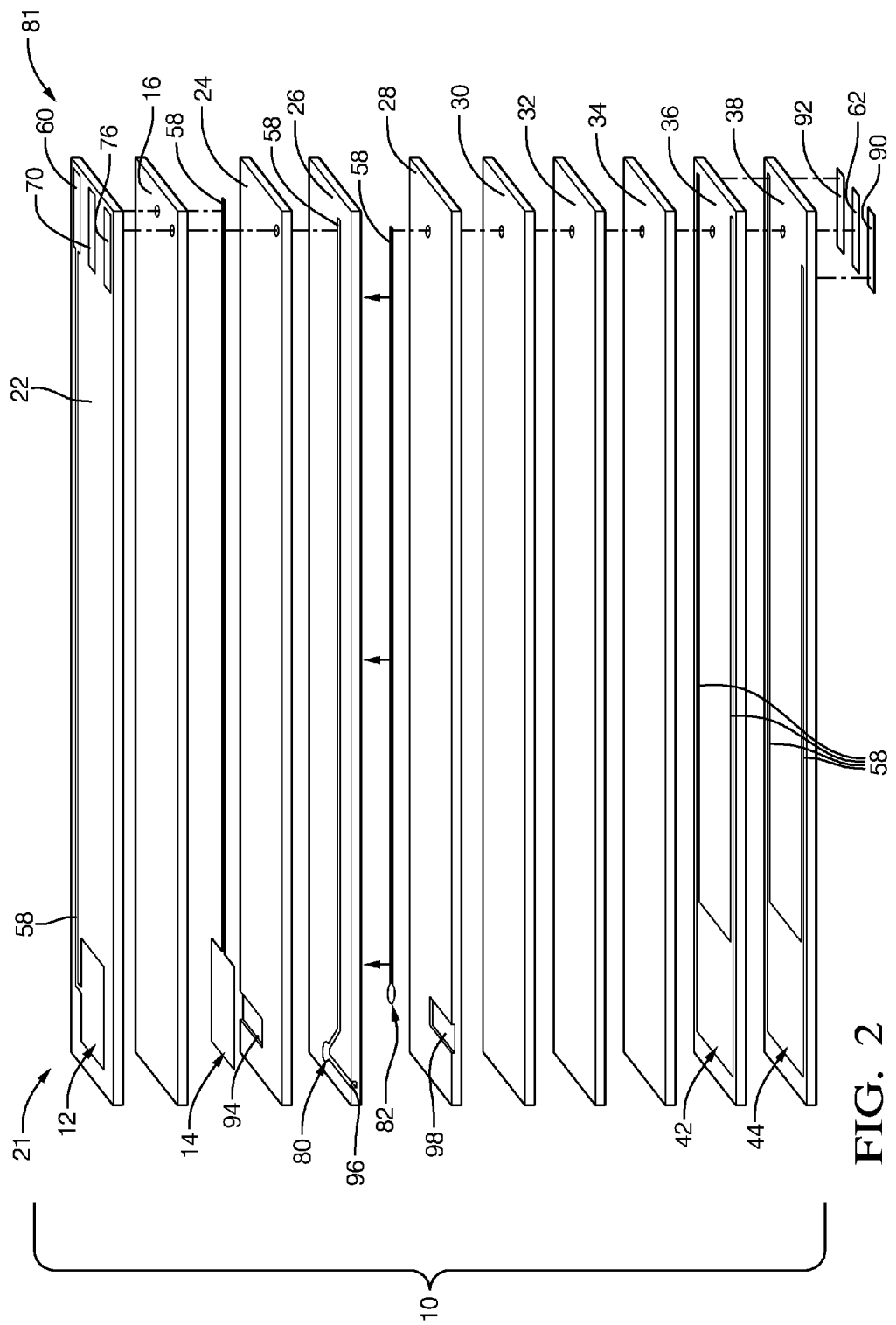
FIG. 2 is an exploded view of an exemplary embodiment of a NO$_2$ sensor including a NO$_2$ sensing element.

Referring now to the FIG. 2, an example embodiment of a $NO_2$ sensor 10 comprising the above-described sensing element is schematically depicted. It is to be understood that although the invention is described in relation to a flat plate sensor, other two and three dimensional sensor designs can also be employed, such as conical, cylindrical, and the like, which also employ the arrangement of the elements described herein in a different physical configuration. An exemplary sensing element 10 includes an $NO_2$ sensing cell (12, 16, 14) including a sensing electrode 12, a first reference electrode 14 and an electrolyte layer 16. The $NO_2$ sensing cell 12, 16, 14 is disposed at a sensing end 21 of the sensing element 10. The sensing element 10 includes insulating layers 22, 24, 28, 30, 32, 34, 36, 38, and active layers, which include the electrolyte layer 16 and layer 26. The active layers can conduct oxygen ions, where the insulating layers can insulate sensor components from electrical and ionic conduction. In an exemplary embodiment, the electrolyte layer 16 is disposed between insulating layers 22 and 24, and active layer 26 is disposed between insulating layers 24 and 28.

The sensing element 10 can further include a temperature sensor (not shown), an air-fuel sensing cell comprising the active layer 26 along with an electrode 80 and an electrode 82 (80/26/82), a heater 44 disposed between the insulating layers 36 and 38, and an electromagnetic shield 42 (also known as a ground plane layer) disposed between the insulating layers 34 and 36. A first inlet 94 is defined by a first surface of the insulating layer 24 and by a surface of the electrolyte 16, proximate the first reference electrode 14. A second inlet 96 is defined by a first surface of the active layer 26 and a second surface of the insulating layer 24, proximate the electrode 80. A third inlet 98 is defined by a second surface of the active layer 26 and a first surface of the insulating layer 28, proximate the electrode 82. In addition, the sensing element 10 includes electrical leads 58, contact pads 60, 62, 70, 76, 90, 92, and may include additional ground plane layer(s) (not shown), and the like.

The sensing electrode 12 is disposed in physical and ionic communication with electrolyte 16 and can be disposed in fluid communication with a sample gas (e.g., a gas being monitored or tested for its $NO_2$ concentration). Referring to FIG. 2, this physical and ionic communication between electrolyte 16 and sensing electrode 12 may be effected by forming insulating layer 22 with openings corresponding to and located under sensing electrode 12, which extend through insulating layer 22, thereby allowing the sensing electrode material disposed on the top surface of insulating layer 22 to extend through the opening and provide physical and ionic communication with an upper surface of electrolyte 16. In one embodiment, the sensing electrode material may be screen printed onto an assembly of the insulating layer 22 and electrolyte 16 and fired such that it extends through the opening and makes the necessary physical and ionic communication with electrolyte 16. The electrode materials have $NO_2$ sensing capability (e.g., electrochemically catalyzing $NO_2$ gas to produce an emf), electrical conducting capability (conducting electrical current produced by the emf), and gas diffusion capability (providing sufficient open porosity so that gas can diffuse throughout the electrode and to the interface region of the sensing electrode 12 and electrolyte 16.

An air-fuel sensor such as the air-fuel sensing cell (80/26/82 can detect the air to fuel ratio of the sample gas, which allows for a determination to be made of water and oxygen partial pressures for use in Nernst equation calculations. When a constant potential is applied to electrodes 80 and 82, the current through the air-fuel sensing cell 80/26/82 is limited by the oxygen available in the inlets 96, or 98 and at the electrodes 80, 82. Therefore, by measuring the limiting current at the air-fuel sensing cell 80/26/82, the processor can determine the air-to-fuel ratio of the gas. This same cell can also be used for sensing the temperature of the gas. In this mode an AC signal will be applied to the electrode 80 and 82, and the impedance of the electrolyte 26 between the two electrodes 80 and 82 is used for temperature determination.

The heater 44 can be employed to maintain the sensing element 10 at a selected operating temperature. The heater 44 can be positioned as part of the monolithic design of the sensing element 10, for example between insulating layer 36 and insulating layer 38, in thermal communication with the air-fuel sensing cell 80/26/82 and the NO$_2$ sensing cell 12/16/14. In other embodiments, the heater could be in thermal communication with the cells without necessarily being part of a monolithic laminate structure with them, e.g., simply by being in close physical proximity to a cell. More specifically, the heater can be capable of maintaining the sensing end 21 of the sensing element 10 at a sufficient temperature to facilitate the various electrochemical reactions therein. The heater can be a resistance heater and can comprise a line pattern (connected parallel lines, serpentine, and/or the like (not shown)). The heater can comprise, for example, platinum, aluminum, palladium, and the like, as well as combinations comprising at least one of the foregoing, oxides comprising at least one of the foregoing metals. Contact pads, for example, the fourth contact pad 90 and the fifth contact pad 92, can transfer current to the heater from an external power source.

The temperature sensor (not shown) comprises any temperature sensor capable of monitoring the temperature of the sensing end 21 of the sensing element 10 such as, for example, an impedance-measuring device or a metal-like resistance-measuring device. The metal-like resistance temperature sensor can comprise, for example, a line pattern (connected parallel lines, serpentine, and/or the like). Some possible materials include, but are not limited to, electrically conductive materials such as metals including platinum (Pt), copper (Cu), silver (Ag), palladium (Pd), gold (Au), tungsten (W), as well as combinations comprising at least one of the foregoing.

Disposed between the insulating layers 34 and 36 can be an electromagnetic shield 42. The electromagnetic shield 42 isolates electrical influences by dispersing electrical interferences and creating a barrier between a high power source (such as the heater) and a low power source (such as the air-fuel ratio sensor, the temperature sensor, and the gas sensing cell). The shield can comprise, for example, a line pattern (connected parallel lines, serpentine, cross hatch pattern, and/or the like). Any suitable electrically conductive material may be used. Some possible materials for the shield can include, without limitation, those materials discussed above for the heater or temperature sensor.

At the sensing end 21 of the sensing element 10, the electrical leads 58, are disposed in physical contact and in electrical communication with electrodes 12, 14, 80, 82. In an exemplary embodiment, electrodes 80 and 82 and their associated electrical leads are disposed on an upper and a lower surface of electrolyte 26. Further, electrical leads 58 are disposed in electrical communication with the heater 44 and the electromagnetic shield 42. Each electrical lead extends from a contact pad or via toward the sensing end 21. Electrical leads not disposed on a top surface or a bottom surface of the sensing element 10 are in electrical communication with the contact pads through vias formed in the layers. Two sets of three contact pads are disposed at the terminal end 81 of the sensing element 10: the first, second, and third contact pads 60, 70, 76, respectively, are disposed on the upper surface of the sensing element 10, and the fourth, fifth and sixth contact pads 62, 90, 92, respectively, are disposed on the lower surface of the sensing element 10. The first, second, third, and fourth contact pads 60, 62 70, 76 are in electrical communication with a controller (not shown), and the fifth and sixth contact pads 90, 92 are in electrical communication with an external power source (not shown) which may also be incorporated into or associated with a controller or controllers, including various microprocessor-based controllers.

The insulating layers 22, 24, 2 30, 32, 34, 36, 38 can comprise a dielectric material such as alumina (i.e., aluminum oxide $Al_2O_3$), other insulating ceramics, and the like. Each of the insulating layers can comprise a sufficient thickness to attain the desired insulating and/or structural properties. For example, each insulating layer can have a thickness of about 1 up to about 200 micrometers or so, depending upon the number of layers employed, or, more specifically, a thickness of about 50 micrometers to about 200 micrometers. Further, the sensor element 10 can comprise additional insulating layers to isolate electrical devices, segregate gases, and/or to provide additional structural support.

The active layer 26 can include material that, while under the operating conditions of sensing element 10, is capable of permitting the electrochemical transfer of oxygen ions. These include the same or similar materials to those described as comprising electrolyte layer 16. Each of the active layers can comprise a thickness of up to about 200 micrometers or so, depending upon the number of layers employed, or, more specifically, a thickness of about 50 micrometers to about 200 micrometers.

The sensing element 10 and the layers and components thereof can be formed using any suitable method, including various ceramic processing techniques. For example, milling processes (e.g., wet and dry milling processes including ball milling, attrition milling, vibration milling, jet milling, and the like) can be used to size ceramic powders into desired particle sizes and desired particle size distributions to obtain physical, chemical, and electrochemical properties. The ceramic powders can be mixed with plastic binders to form various shapes. For example, the structural components (e.g., insulating layers 22, 24, 28, 30, 32, 34, 36, and 38 and the active or electrolyte layers 16, 26) can be formed into "green" tapes by tape-casting, role-compacting, or similar processes. The non-structural components (e.g., the sensing electrode 12, the reference electrode 14, the electrical leads, and the contact pads) can be formed into a tape or can be deposited onto the structural components by any suitable method, including various ceramic processing techniques (e.g., sputtering, painting, chemical vapor deposition, screen-printing, stenciling, and the like).

The inlets 94, 96, 98, can be formed either by disposing fugitive material (material that will dissipate during the sintering process, e.g., graphite, carbon black, starch, nylon, polystyrene, latex, other insoluble organics, as well as compositions comprising one or more of the foregoing fugitive materials) or by disposing material that will leave sufficient open porosity in the fired ceramic body to allow gas diffusion therethrough. Once the "green" sensor is formed, the sensor can be sintered at a selected firing cycle to allow controlled burn-off of the binders and other organic materials and to form the ceramic material of the sensor with the desired physical, microstructural, compositional and other properties described herein.

The temperature sensor can measure a temperature indicative of the absolute gas temperature (T). The oxygen and water vapor content, e.g., partial pressures, in the unknown gas can be determined from the air-fuel ratio as measured by the air-fuel sensing cell 80/26/82.

The air to fuel ratio can be obtained by a controller (not shown), such as an engine control module (ECM) as described, for example in GB2347219A, or by having an air to fuel ratio sensor integrated into the sensor 10 as shown in FIG. 2. Alternatively, a complete mapping of $H_2O$ and $O_2$ concentrations under all engine running conditions (measured by instruments such as mass spectrometer) can be obtained empirically and stored in the ECM or in a memory chip (e.g., EEPROM) on-board with the sensor assembly a look-up table with which the sensor is in signal communication. Other data such as $NO_2$ calibration parameters can also be stored in on-board memory locally at the sensor assembly. Once the oxygen and water vapor content information is known, the controller can use the information to more accurately determine the partial pressures of the sample gas components.

In some embodiments, the $NO_2$-sensing element can be integrated in a sensor assembly as an $NO_2$-sensing cell along with a separate ammonia-sensing cell. Examples of materials and components for sensors having ammonia-sensing cells and $NO_2$-sensing cells are described in U.S. Pat. No. 7,074,319 B2, the disclosure of which is incorporated herein by reference in its entirety.

In some example embodiments, one or more of the components, including but not limited to the $NO_2$ sensing element, the temperature sensor, the heater, an ammonia sensor, or an air-fuel sensor, a protective layer can be included in to provide protection from the effects of poisons in the exhaust gas. Examples of materials for such protective layers include, but are not limited to porous, high-surface area alumina-based oxides with oxide glassy binders. The protective layer can be formed by mixing alumina powder with a glass powder (e.g., alkali oxide-alumina-borosilicate glass and the like). This protective layer can be implemented by coating the $NO_2$ sensing electrode and/or other electrodes by screening printing, painting, or jetting methods, or the coating can be done by dipping the tip of the sensing element into the coating slurry. After application, the coating can be optionally dried, and is then fired to fuse the glass powder into a solid material.

Figure 3:
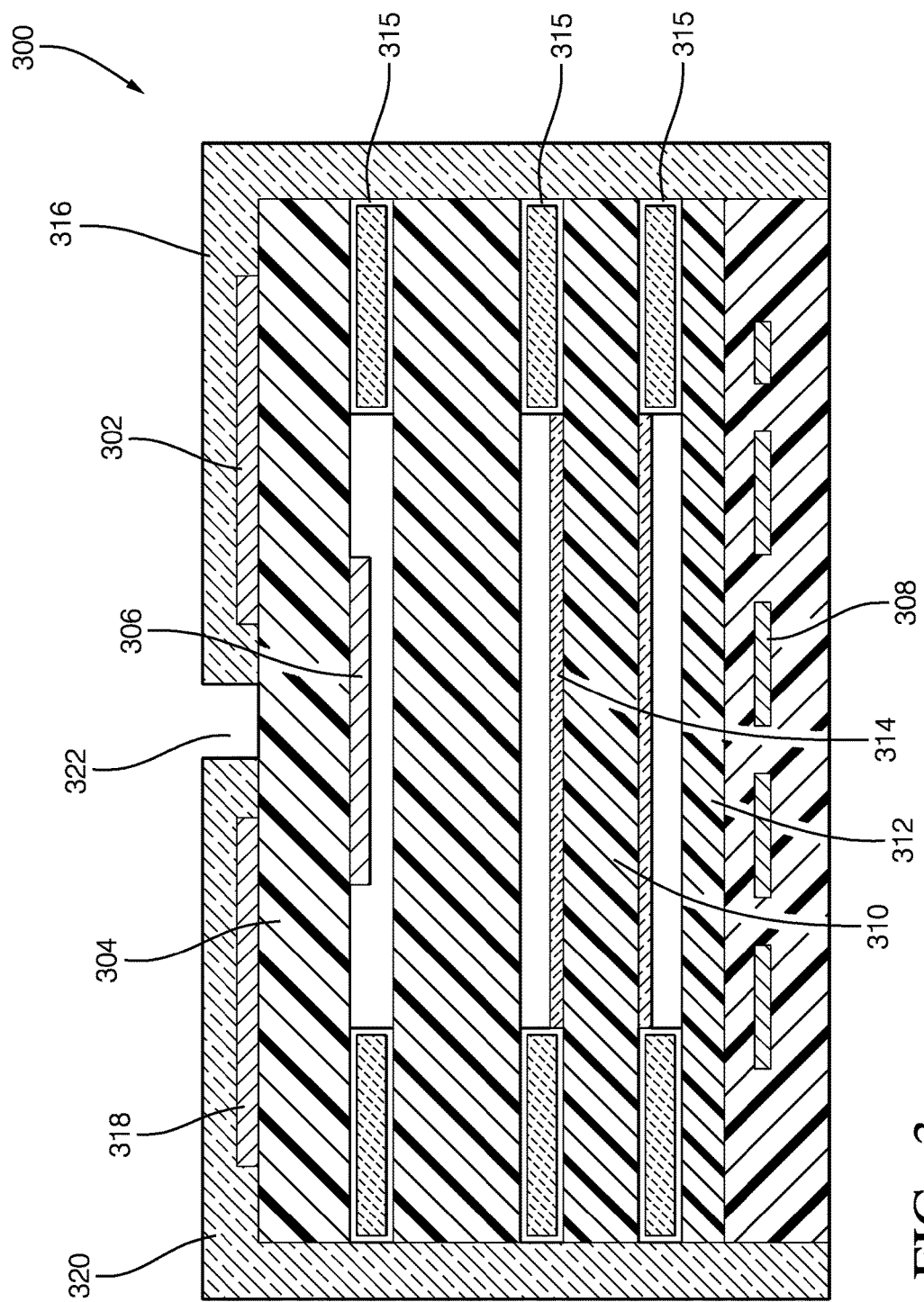
FIG. 3 is a cross-sectional view of an exemplary embodiment of a NO$_2$ and NH$_3$ sensing element with posion protection coating layers.
Figure 4:
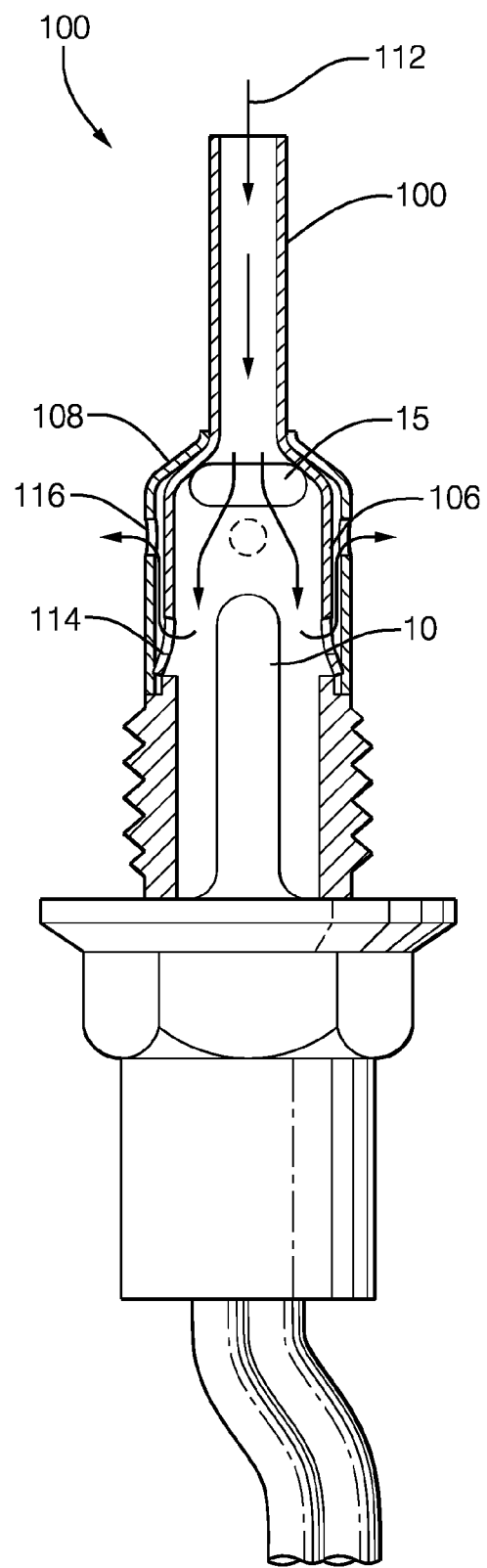
FIG. 4 is a cross-sectional view of an exemplary embodiment of a gas sensor assembly that includes a NO$_2$ sensor and sensing element.

An example embodiment that includes a protective layer is schematically depicted in FIG. 3. As shown in FIG. 3, a sensor assembly 300 includes a $NO_2$ sensing cell comprising $NO_2$ sensing electrode 302, electrolyte 304, and reference electrode 306. The sensor assembly 300 also includes a heater 308 and a temperature sensing cell that comprises an electrolyte 310 and electrodes 312/314. Gas apertures 315 provide gas to the various cells. As further shown in FIG. 3, the $NO_2$ sensing electrode 302 is covered by a protective layer 316 as described above. The sensor assembly 300 also includes a $NH_3$ sensing cell comprising $NH_3$ sensing electrode 318, electrolyte 304, and reference electrode 306. As further shown in FIG. 3, the $NH_3$ sensing electrode is covered by a protective layer 320 as described above. The separation 322 between the protective layers 316 and 320 can help promote resistance to cross-talking between the emf signal of difference gas sensing cells that may occur if the cells are connected by the protective layer, as it has been discovered that the protective layers can have mixed ionic and electronic conductivity at elevated temperatures. The separation 322 can be provided by separately applying the protective layers, e.g. by separately screening printing, painting, or jet application. Alternatively, the separation 322 can be provided by physical removal of a portion of the coating (e.g., by scratching) after dipping the tip of the sensing element into the coating slurry and drying/firing of the coating layer. In some embodiments, the protective layers can be applied to portions of the sensor assembly besides the sensing electrodes, as schematically depicted on the left hand and right hand sides of the assembly 300. Some areas of gas exposure, however, may go without protective layers. For example, the area where porous gas apertures meet the surface of the sensing element may not need the coating layer for poison protection, this is because the gas apertures can provide the same protection feature by themselves Referring now to FIG. 4, a sensor assembly 100 for placement in a gas stream can include a gas sensor 10 (FIG. 2) disposed within a protective casing. The protective casing can comprise an outer shield 108 having a plurality of outer shield holes 116, and an inner shield 106 having a plurality of passages 114, which allow fluid to enter a space between the inner shield 106 and the outer shield 108. Outer shield holes 116 allow fluid in the space between inner shield 106 and outer shield 108 to exit the casing. The protective casing can also include an optional sampling tube 110 having an inlet 112 extending from the outer shield 108. Arrows are shown to illustrate the general fluid flow direction within the protective casing.

The plurality of exhaust passages 114 may be disposed through inner shield 106 to allow the exhaust fluid a sufficient time to contact the sensing element 10 prior to exiting the protective casing. The plurality of exhaust passages 114 can be any size or shape sufficient to allow the passage of exhaust fluid.

Suitable materials for the protective casing can include materials that are capable of resisting under-car salt and other contaminants, operating temperatures, and corrosion. For example, ferrous materials are employed including various stainless steels, such as ferritic stainless steels. Ferritic stainless steels may include stainless steels such as, e.g., SS-409, SS-316, and the like.

A catalyst 15 can be disposed in the exhaust stream, upstream from the sensing element 10. The catalyst 15 can include a material that, under the operating conditions of sensing element 10, is capable of efficiently converting NO to $NO_2$. In a second embodiment, the catalyst 15 includes a material that, under the operating conditions of the sensing element 10 is capable of converting $NO_2$ to NO. The catalyst 15 can comprise materials including platinum, platinum alloys, and the like, as well as combinations comprising at least one of the foregoing. The catalyst 15 can further comprise zeolite(s) (e.g., alumina-silica zeolite powder).

The catalyst 15 can be disposed proximate various locations in the casing. In general, the catalyst 15 can be disposed at a location in which the sample gas can sufficiently contact the catalyst 15 upstream from the sensing element 10. For example the catalyst 15 can be disposed proximate the sampling tube 110 or can be disposed proximate the inner surface of the inner shield 106. The catalyst 15 can also be disposed outside the casing upstream from the sensing element 10. For example, the catalyst 15 could be part of a catalyst bed reactor, upstream from the inlet 112 of the casing. In an exemplary embodiment, the sensing element 10 is disposed in an exhaust stream in fluid communication with engine exhaust.

The following examples are intended to further describe the $NO_2$ sensor and electrodes thereof and not to limit the present disclosure.

EXAMPLES

Example 1

The composition of the sensor material in this example was $(MnMgSiO_4)+0.0125(Mn_3Al_2Si_3O_{12})+0.0250(SiO_2)$. It is made of MnO, MgO, $Al_2O_3$ and $SiO_2$ powders, mechanically mixed and fired at 1250 C in air for fifteen hours to produce a powder of an oxide having the chemical composition indicated above. The oxide was formulated into a thick film ink as described herein, printed onto the surface of a electrolyte layer as described herein, fired at 1000 C for one hour in air, and assembled into a sensor element as described herein. The sensor element was fabricated into an $NO_2$ sensor as described herein. The $NO_2$ sensor was used to make emf measurements at several concentrations of $NH_3$, NO, $NO_2$ in order to evaluate the performance of the sensor elements and, more particularly, the performance of the oxide material described above as an $NO_2$ sensor material and its sensitivity to other gases.

The following Table 1 shows emf outputs at baseline and at individual gas dosing condition of 100 ppm NH3, 400 ppm NO and 400 ppm $NO_2$. It is obvious that the absolute values of emf output caused by $NH_3$ and NO are much smaller than that by $NO_2$.

TABLE 1

| Sample | T08_03_emf1 |
|---|---|
| Oxides | (MnMgSiO4) + 0.0125(Mn3Al2Si3O12) + 0.0250(SiO2) |
| Test # | P58348_13_07 |
| emf unit | mV |
| Base Line | 2 |
| NH3_100 ppm | −3 |
| NO_400 ppm | −5 |
| NO2_400 ppm | 55 |

Figure 5:
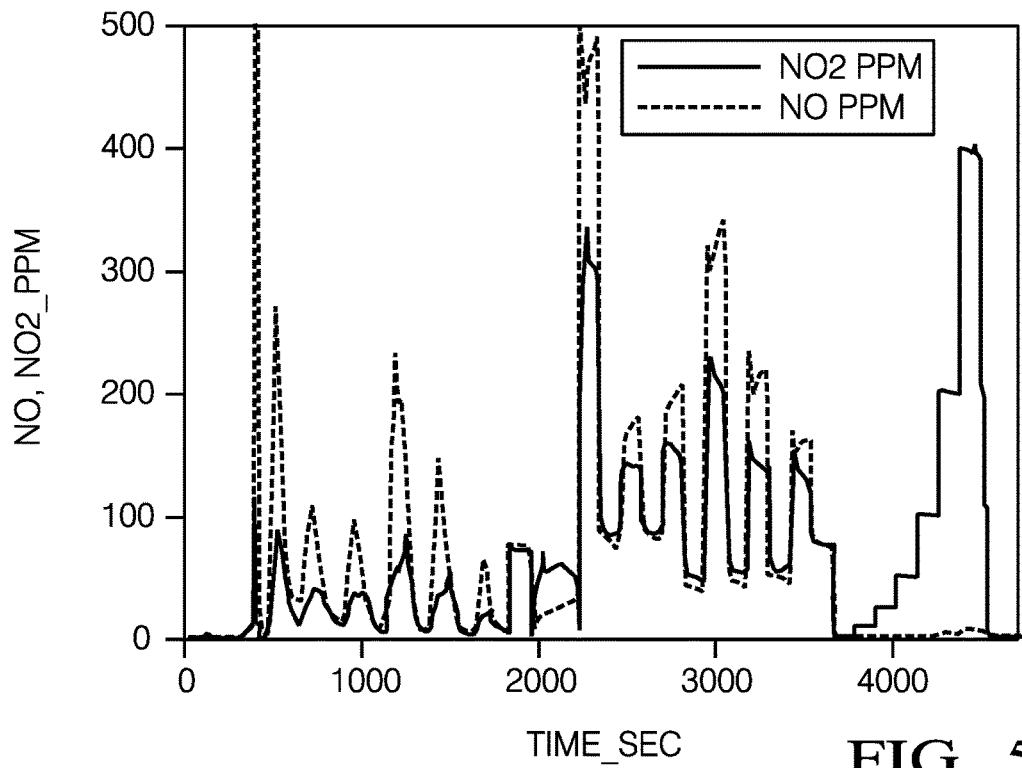
FIG. 5 is a graphical representation of NO$_2$ concentration (solid curve) and NO concentration (dash curve) measured using laboratory FTIR instrumentation during an engine test cycle.
Figure 6:
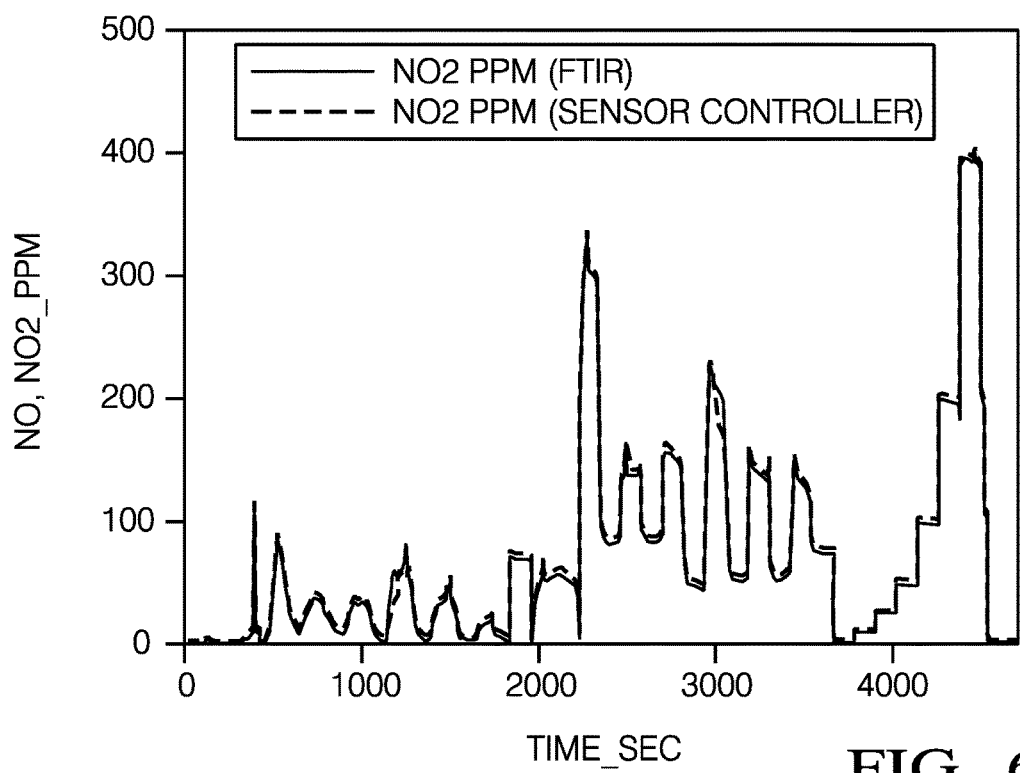
FIG. 6 is a graphical representation of NO$_2$ concentration measured using laboratory FUR instrumentation (solid curve), and NO$_2$ concentration as indicated by a sensor incorporating aspects of the present invention (light dash curve), during an engine test cycle.

The sensor was tested in an engine test cell with the engine produced an exhaust gas with NO and $NO_2$ distribution plotted in FIG. 5, both NO (dotted line) and $NO_2$ (solid line) concentrations were measured by Fourier transform infrared spectroscopy (FTIR) test cell instrumentation. The step sweep $NO_2$ data shown in this figure (after 4000 sec) were used to calibrate the sensor for converting emf output to $NO_2$ in ppm (this conversions were carried out by an electronic processor inside the sensor controller). The $NO_2$ outputs in ppm from the sensor controller (dashed line) plotted against FTIR $NO_2$ data (solid line) in FIG. 6, and show that both data are matched well to each other.

Example 2

The composition of the sensor material in this example was $(MnCoSiO_4)+0.0125(Mn_3Al_2Si_3O_{12})+0.0250(SiO_2)$. It is made of MnO, $Co_3O_4$, $Al_2O_3$ and $SiO_2$ powders, mechanically mixed and fired at 1275 C in air for fifteen hours to produce a powder of an oxide having the chemical composition indicated above. The oxide was formulated into a thick film ink as described herein, printed onto the surface of a electrolyte layer as described herein, fired at 1000 C for one hour in air, and assembled into a sensor element as described herein. The sensor element was fabricated into an $NO_2$ sensor as described herein. The $NO_2$ sensor was used to make emf measurements at several concentrations of $NH_3$, NO, $NO_2$ in order to evaluate the performance of the sensor elements and, more particularly, the performance of the oxide material described above as an $NO_2$ sensor material and its sensitivity to other gases.

The following Table 2 shows emf outputs at baseline and at individual gas dosing condition of 100 ppm $NH_3$, 400 ppm NO and 400 ppm $NO_2$. It is obvious that the absolute values of emf output caused by $NH_3$ and NO are much smaller than that by $NO_2$. Further testing the sensor at an engine test cell showed results similar to FIG. 6 of Example 1

TABLE 2

| Sample | T08_35_emf1 |
|---|---|
| Oxides | (MnCoSiO4) + 0.0125(Mn3Al2Si3O12) + 0.0250(SiO2) |
| Test # | P58348_14_17 |
| emf unit | mV |
| Base Line | 4 |
| NH3_100 ppm | −8 |
| NO_400 ppm | −8 |
| NO2_400 ppm | 78 |

Example 3

The composition of the sensor material in this example was $(Mn_{1.6}Mg_{0.4}SiO_4)+0.2000(Mn_3Al_2Si_3O_{12})+0.0250(SiO_2)$. It is made of MnO, MgO, $Al_2O_3$ and $SiO_2$ powders, mechanically mixed and fired at 1185° C. in air for fifteen hours to produce a powder of an oxide having the chemical composition indicated above. The oxide was formulated into a thick film ink as described herein, printed onto the surface of a electrolyte layer as described herein, fired at 1000° C. for one hour in air, and assembled into a sensor element as described herein. The sensor element was fabricated into an $NO_2$ sensor as described herein. The $NO_2$ sensor was used to make emf measurements at several concentrations of $NH_3$, NO, $NO_2$ in order to evaluate the performance of the sensor elements and, more particularly, the performance of the oxide material described above as an $NO_2$ sensor material and its sensitivity to other gases.

The following Table 3 shows emf outputs at baseline and at individual gas dosing condition of 100 ppm $NH_3$, 400 ppm NO and 400 ppm $NO_2$. It is obvious that the absolute values of emf output caused by $NH_3$ and NO are much smaller than that by $NO_2$. Further testing the sensor at an engine test cell showed results similar to FIG. 6 of Example 1.

TABLE 3

| Sample | T11_03_emf2 |
|---|---|
| Oxides | (Mn1.6Mg0.4SiO4) + 0.2000(Mn3Al2Si3O12) + 0.0250(SiO2) |
| Test # | P58348_15_08 |
| emf unit | mV |
| Base Line | 2 |
| NH3_100 ppm | −9 |
| NO_400 ppm | −4 |
| NO2_400 ppm | 58 |

Example 4

The composition of the sensor material in this example was $(Mn_{1.14}Mg_{0.18}Co_{0.68}SiO_4)+0.0000(Mn_3Al_2Si_3O_{12})+0.025(SiO_2)$. It is made of MnO, MgO, $Co_3O_4$, $Al_2O_3$ and $SiO_2$ powders, mechanically mixed and fired at 1250° C. in air for fifteen hours to produce a powder of an oxide having the chemical composition indicated above. The oxide was formulated into a thick film ink as described herein, printed onto the surface of a electrolyte layer as described herein, fired at 1000° C. for one hour in air, and assembled into a sensor element as described herein. The sensor element was fabricated into an $NO_2$ sensor as described herein. The $NO_2$ sensor was used to make emf measurements at several concentrations of $NH_3$, NO, $NO_2$ in order to evaluate the performance of the sensor elements and, more particularly, the performance of the oxide material described above as an $NO_2$ sensor material and its sensitivity to other gases.

The following Table 4 shows emf outputs at baseline and at individual gas dosing condition of 100 ppm $NH_3$, 400 ppm NO and 400 ppm $NO_2$. It is obvious that the absolute values of emf output caused by $NH_3$ and NO are much smaller than that by $NO_2$. Further testing the sensor in an engine test cell showed results similar to FIG. 6 of Example 1.

TABLE 4

| Sample | MT05_12_emf1 |
|---|---|
| Oxides | (Mn1.14Mg0.18Co0.68SiO4) + 0.0000(Mn3Al2Si3O12) + 0.0250(SiO2) |
| Test # | P58348_07_14 |
| emf unit | mV |
| Base Line | 2 |
| NH3_100 ppm | −7 |
| NO_400 ppm | −6 |
| NO2_400 ppm | 69 |

Example 5

The composition of the sensor material in this example was $(Mn_{1.5}Co_{0.5}SiO_4)+0.0500(Mn_3Al_2Si_3O_{12})+0.0250(SiO_2)$. It is made of MnO, $Co_3O_4$, $Al_2O_3$ and $SiO_2$ powders, mechanically mixed and fired at 1200° C. in air for fifteen hours to produce a powder of an oxide having the chemical composition indicated above. The oxide was formulated into a thick film ink as described herein, printed onto the surface of a electrolyte layer as described herein, fired at 1000° C. for one hour in air and assembled into a sensor element as described herein. The sensor element was fabricated into an $NO_2$ sensor as described herein. The $NO_2$ sensor was used to make emf measurements at several concentrations of $NH_3$, NO, $NO_2$ in order to evaluate the performance of the sensor elements and, more particularly, the performance of the oxide material described above as an $NO_2$ sensor material and its sensitivity to other gases.

The following Table 5 shows emf outputs at baseline and at individual gas dosing condition of 100 ppm $NH_3$, 400 ppm NO and 400 ppm $NO_2$. It is obvious that the absolute values of emf output caused by $NH_3$ and NO are much smaller than that by $NO_2$. Further testing the sensor in an engine test cell showed results similar to FIG. 6 of Example 1.

TABLE 5

| Sample | MT05_20_emf1 |
|---|---|
| Oxides | (Mn1.5Co0.5SiO4) + 0.0500(Mn3Al2Si3O12) + 0.0250(SiO2) |
| Test # | P58348_07_09 |
| emf unit | mV |
| Base Line | 5.5 |
| NH3_100 ppm | −13 |
| NO_400 ppm | −13 |
| NO2_400 ppm | 75 |

Example 6

The composition of the sensor material in this example was $(MnMgSiO_4)+0.0250(ZnO)+0.0250(SiO_2)$. It is made of MnO, MgO, ZnO and $SiO_2$ powders, mechanically mixed and fired at 1350° C. in air for fifteen hours to produce a powder of an oxide having the chemical composition indicated above. The oxide was formulated into a thick film ink as described herein, printed onto the surface of a electrolyte layer as described herein, fired at 1000° C. for one hour in air, and assembled into a sensor element as described herein. The sensor element was fabricated into an $NO_2$ sensor as described herein. The $NO_2$ sensor was used to make emf measurements at several concentrations of $NH_3$, NO, $NO_2$ in order to evaluate the performance of the sensor elements and, more particularly, the performance of the oxide material described above as an NO2 sensor material and its sensitivity to other gases.

The following Table 6 shows emf outputs at baseline and at individual gas dosing condition of 100 ppm $NH_3$, 400 ppm NO and 400 ppm $NO_2$. It is obvious that the absolute values of emf output caused by $NH_3$ and NO are much smaller than that by $NO_2$. Further testing the sensor in an engine test cell showed results similar to FIG. 6 of Example 1.

TABLE 6

| Sample | T13_13_emf |
|---|---|
| Oxides | (MnMgSiO4) + 0.0250(ZnO) 0.0250(SiO2) |
| Test # | A1832_# |
| emf unit | mV |
| Base Line | 0 |
| NH3_100 ppm | −9 |
| NO_400 ppm | −15 |
| NO2_400 ppm | 58 |

Example 7

The composition of the sensor material in this example was $(MnCoSiO_4)+0.0250(ZnO)+0.0250(SiO_2)$. It is made of MnO, $Co_3O_4$, ZnO and $SiO_2$ powders, mechanically mixed and fired at 1275 C in air for fifteen hours to produce a powder of an oxide having the chemical composition indicated above. The oxide was formulated into a thick film ink as described herein, printed onto the surface of a electrolyte layer as described herein, fired at 1000 C for one hour in air, and assembled into a sensor element as described herein. The sensor element was fabricated into an $NO_2$ sensor as described herein. The $NO_2$ sensor was used to make emf measurements at several concentrations of $NH_3$, NO, $NO_2$ in order to evaluate the performance of the sensor elements and, more particularly, the performance of the oxide material described above as an $NO_2$ sensor material and its sensitivity to other gases.

The following table shows emf outputs at baseline and at individual gas dosing condition of 100 ppm $NH_3$, 400 ppm NO and 400 ppm $NO_2$. It is obvious that the absolute values of emf output caused by $NH_3$ and NO are much smaller than that by $NO_2$. Further testing the sensor in an engine test cell showed results similar to FIG. 6 of Example 1.

TABLE 7

| Sample | T13_01_emf1 |
|---|---|
| Oxides | (MnCoSiO4) + 0.0250(ZnO) + 0.0250(SiO2) |
| Test # | A1830_#5 |
| emf unit | mV |
| Base Line | 1 |
| NH3_100 ppm | −13 |
| NO_400 ppm | −16 |
| NO2_400 ppm | 57 |

Example 8

The composition of the sensor material in this example was $(MnCoSiO_4)+0.0250(ZnO)+0.0125(Mn_3Al_2Si_3O_{12})+0.0250(SiO_2)$. It is made of MnO, $Co_3O_4$, ZnO, $Al_2O_3$, and $SiO_2$ powders, mechanically mixed and fired at 1325° C. in air for fifteen hours to produce a powder of an oxide having the chemical composition indicated above. The oxide was formulated into a thick film ink as described herein, printed onto the surface of a electrolyte layer as described herein, fired at 1000° C. for one hour in air, and assembled into a sensor element as described herein. The sensor element was fabricated into an $NO_2$ sensor as described herein. The $NO_2$ sensor was used to make emf measurements at several concentrations of $NH_3$, NO, $NO_2$ in order to evaluate the performance of the sensor elements and, more particularly, the performance of the oxide material described above as an $NO_2$ sensor material and its sensitivity to other gases.

The following table shows emf outputs at baseline and at individual gas dosing condition of 100 ppm $NH_3$, 400 ppm NO and 400 ppm $NO_2$. It is obvious that the absolute values of emf output caused by $NH_3$ and NO are much smaller than that by $NO_2$. Further testing the sensor in an engine test cell showed results similar to FIG. 6 of Example 1.

TABLE 8

| Sample | T12_34_emf1 |
|---|---|
| Oxides | (MnMgSiO4) + 0.0250(ZnO) + 0.0125(Mn3Al2SiO12) + 0.0250(SiO2) |
| Test # | A1830_#3 |
| emf unit | mV |
| Base Line | 0 |
| NH3_100 ppm | −6 |
| NO_400 ppm | −9 |
| NO2_400 ppm | 50 |

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

The invention claimed is:

1. A $NO_2$ gas sensing element, comprising:
   an electrolyte;
   a reference electrode in contact with the electrolyte; and
   a sensing electrode selective to $NO_2$ in contact with the electrolyte spaced apart from the reference electrode, the $NO_2$ selective sensing electrode comprising an oxide material comprising:
   (1) a mixed oxide according to the formula $(Mn_{2-u-v-w}Co_vMg_wSiO_{4-u})+\xi(Mn_3Al_2Si_3O_{12})+\delta(SiO_2)$, wherein $0\leq(u+v+w)\leq2.00$, $0\leq\xi\leq0.5$, and $0\leq\delta\leq0.1$;
   (2) a mixed oxide according to the formula $(Mn_{2-x-y-z}Co_yMg_zSiO_{4-x})+\xi(ZnO)+\delta(SiO_2)$, wherein $0\leq(x+y+z)\leq2.00$, $0\leq\xi\leq0.5$, and $0\leq\delta\leq0.1$; or
   a combination comprising mixed oxides (1) and (2).

2. The sensing element of claim 1, wherein the composition comprises the mixed oxide (1).

3. The sensing element of claim 2, wherein $0.75\leq(u+v+w)\leq1.25$, $0\leq\xi\leq0.025$, and $0\leq\delta\leq0.050$.

4. The sensing element of claim 1, wherein the composition comprises the mixed oxide (2).

5. The sensing element of claim 4, wherein $0.75\leq(x+y+z)\leq1.25$, $0\leq\xi\leq0.025$, and $0\leq\delta\leq0.050$.

6. The sensing element of claim 1, wherein the composition comprises the mixed oxide (1) and the mixed oxide (2).

7. The sensing element of claim 6, wherein $0.75\leq(u+v+w)\leq1.25$, $0\leq\xi\leq0.025$, and $0\leq\delta\leq0.050$.

8. The sensing element of claim 6, wherein $0.75\leq(x+y+z)\leq1.25$, $0\leq\xi\leq0.025$, and $0\leq\delta\leq0.050$.

9. The sensing element of claim 6, wherein $0.75\leq(u+v+w)\leq1.25$, $0\leq\xi\leq0.025$, and $0\leq\delta\leq0.050$; and $0.75\leq(x+y+z)\leq1.25$, $0\leq\xi\leq0.025$, and $0\leq\delta\leq0.050$.

10. The sensing element of claim 1, wherein the electrolyte comprises a solid oxide.

11. The sensing element of claim 10, wherein the solid oxide comprises zirconia, ceria, lanthanum gallates, or mixtures comprising any of the foregoing.

12. The sensing element of claim 1, further comprising a protective coating layer covering the sensing electrode.

13. The sensing element of claim 12, wherein the protective coating comprises high surface area alumina-based oxide particles in an oxide glassy binder.

14. A method of detecting $NO_2$, comprising contacting a test gas with the reference and sensing electrodes of a sensing element according to claim 1, and measuring a voltage signal between the sensing electrode and the reference electrode.

15. A $NO_2$ sensor assembly comprising a heating cell, a temperature-sensing cell, and an electrochemical $NO_2$ sensing cell comprising the $NO_2$ sensing element of claim 1 and an electrical circuit connection between the reference electrode and the sensing electrode and configured to contact the reference and sensing electrodes with test gas.

16. The $NO_2$ sensor assembly of claim 15, further comprising a protective layer, on the $NO_2$-sensing electrode.

17. The $NO_2$ sensor assembly of claim 15, further comprising an air-fuel sensing cell, an ammonia-sensing cell, or an air-fuel sensing cell and an ammonia-sensing cell.

18. The $NO_2$ sensor assembly of claim 17, wherein the ammonia-sensing cell includes an ammonia sensing electrode and an ammonia reference electrode, and wherein sensing electrodes of the $NO_2$-sensing cell and the ammonia-sensing cell are each covered by separate protective layers.

19. The $NO_2$ sensor assembly of claim 17, further comprising an electronic memory chip containing stored calibration factors for any one or combination of the temperature-sensing cell, the $NO_2$ sensing cell, the air-fuel sensing cell, and the ammonia-sensing cell.

20. A combustion exhaust system, comprising the $NO_2$ sensor assembly of claim 17 disposed to cause the $NO_2$ sensing cell to provide contact of the reference and sensing electrodes with a source of combustion exhaust gas, and an electronic controller in contact with the heating cell, the temperature-sensing cell, and the electrochemical $NO_2$ sensing cell; the electronic controller configured to provide close-loop control of the heating cell based on temperature-sensing cell output, and/or to convert emf data from the $NO_2$ sensing cell electrical circuit to $NO_2$ concentration value.

* * * * *